(12) United States Patent
Amonette et al.

(10) Patent No.: US 6,873,415 B2
(45) Date of Patent: Mar. 29, 2005

(54) PHOTOACOUSTIC SPECTROSCOPY SAMPLE ARRAY VESSEL AND PHOTOACOUSTIC SPECTROSCOPY METHOD FOR USING THE SAME

(75) Inventors: James E. Amonette, Richland, WA (US); S. Thomas Autrey, West Richland, WA (US); Nancy S. Foster-Mills, Richland, WA (US); David Green, Dover, MA (US)

(73) Assignee: Battelle Memorial Institute, Richland, WA (US)

( * ) Notice: Subject to any disclaimer, the term of this patent is extended or adjusted under 35 U.S.C. 154(b) by 273 days.

(21) Appl. No.: 10/002,624

(22) Filed: Nov. 13, 2001

(65) Prior Publication Data

US 2003/0090664 A1 May 15, 2003

(51) Int. Cl.[7] ............................................. G01N 21/59
(52) U.S. Cl. ........................................ 356/432; 356/440
(58) Field of Search ................................. 356/432, 436, 356/440, 246

(56) References Cited

U.S. PATENT DOCUMENTS

| | | | | |
|---|---|---|---|---|
| 4,436,428 A | * | 3/1984 | Watanabe et al. | ............ 356/432 |
| 4,738,536 A | * | 4/1988 | Kitamori et al. | ............ 356/441 |
| 5,348,002 A | | 9/1994 | Caro | |
| 5,479,259 A | | 12/1995 | Nakata et al. | |
| 5,492,840 A | | 2/1996 | Malmqvist et al. | |
| 6,191,846 B1 | | 2/2001 | Opsal et al. | |
| 6,236,455 B1 | | 5/2001 | Autrey et al. | |
| 6,244,101 B1 | | 6/2001 | Autrey et al. | |

FOREIGN PATENT DOCUMENTS

| | | |
|---|---|---|
| EP | 0 142 481 | 5/1985 |
| EP | 0 369 176 | 5/1990 |
| JP | 55 010534 | 3/1980 |
| JP | 55 010535 | 3/1980 |
| WO | WO 92 21973 | 10/1992 |
| WO | WO 97 49989 | 12/1997 |
| WO | WO 98 15501 | 4/1998 |
| WO | WO 01 57498 | 8/2001 |

OTHER PUBLICATIONS

Cortese, J., "Technology Improvements are Pushing Microplate Readers into the 21st Century's High–Speed, Computerized World," *The Scientist,* pp. 24–27 (Oct. 2, 2000).

Hamadeh, H. and Afshari, C., "Gene Chips and Functional Genomics: A new Technology Will Allow Environmental Health Scientists to Track the Epxression of Thousands of Genes in a Single, Fast and Easy Test," *American Scientist,* vol. 88, pp. 508–515 (Nov.–Dec. 2000).

(Continued)

*Primary Examiner*—Richard A. Rosenberger
(74) *Attorney, Agent, or Firm*—Klarquist Sparkman, LLP

(57) ABSTRACT

Methods and apparatus for analysis of multiple samples by photoacoustic spectroscopy are disclosed. Particularly, a photoacoustic spectroscopy sample array vessel including a vessel body having multiple sample cells connected thereto is disclosed. At least one acoustic detector is acoustically coupled with the vessel body. Methods for analyzing the multiple samples in the sample array vessels using photoacoustic spectroscopy are provided.

3 Claims, 8 Drawing Sheets

OTHER PUBLICATIONS

Saeks, J., "Biochip Market Experiences Explosive Growth," *Genetic Engineering News,* vol. 21, No. 10 (May 15, 2001).

GeneMachines' OmniGrid™ Accent found at www.genemachines.com/OmniGrid/accent.html.

Packard BioScience's SpotArray Enterprise found at www.packardbioscience.com/products/products.asp?content item id=332.

Packard BioScience's BioChip Arrayer found at www.packardbioscience.com/products/products.asp?content item id=331.

Packard BioScience's SpotArray 24 found at www.packardbioscience.com/products/products.asp?content item id=449.

"Listen to Molecules with Pulsed–Layer Photoacoustics," found at www.qnw.com/photoacoustics.htm.

"The Gas Detection Method: Light into Sound," found at www–tracegasfac.sci.kun.nl/whatis.htm.

Packard Bioscience Company Advertisement, Science, vol. 289, Aug. 18, 2000, Circle No. 16.

Amonette, J.E., Autrey, S.T., Foster–Mills, N.S., Jarman, K.H., Green, D., Norige, M.A. and Bohne, R.D., "Array-Based Photoacoustic Spectroscopy for Environmental and Biomedical Assays," (Mar. 2001).

* cited by examiner

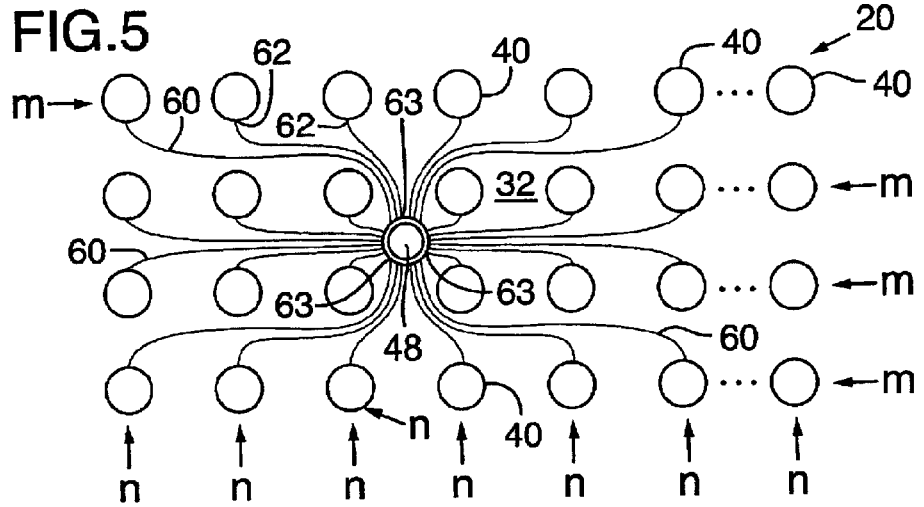
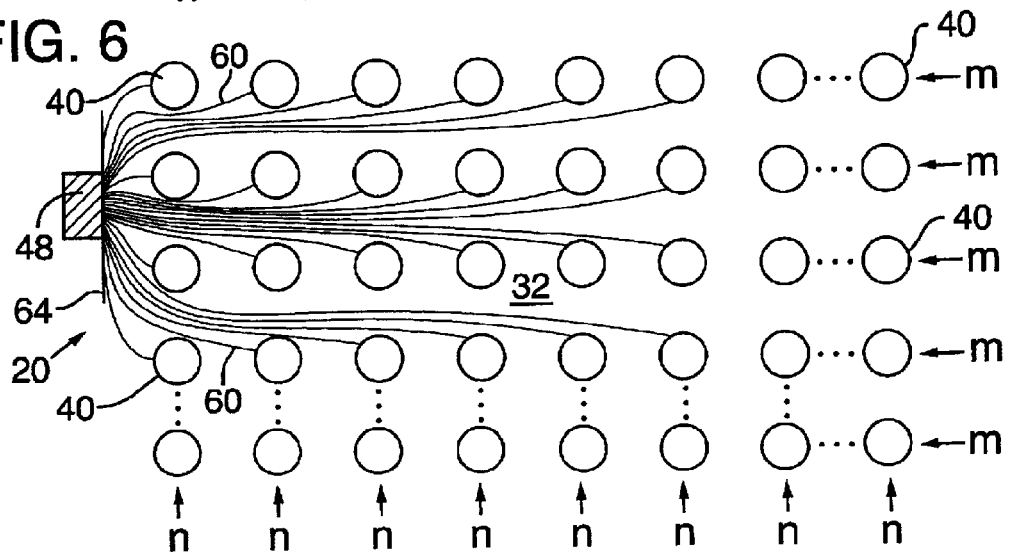
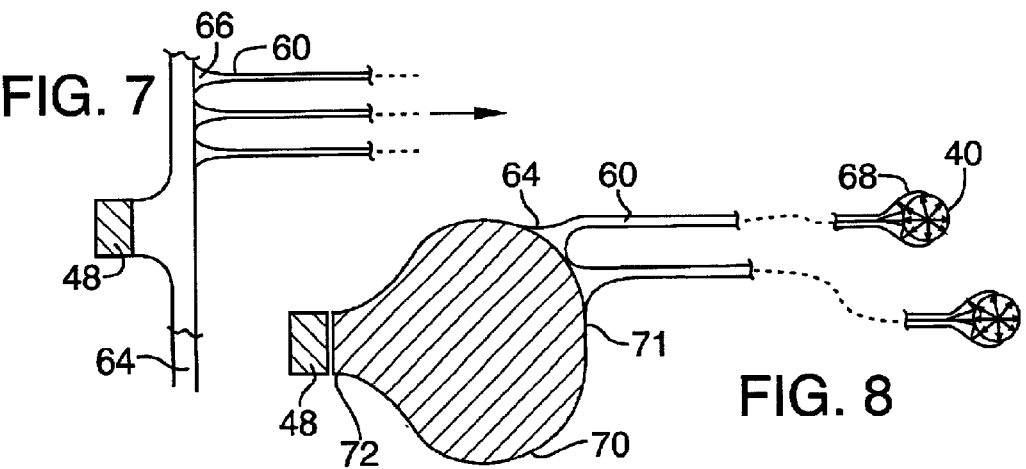

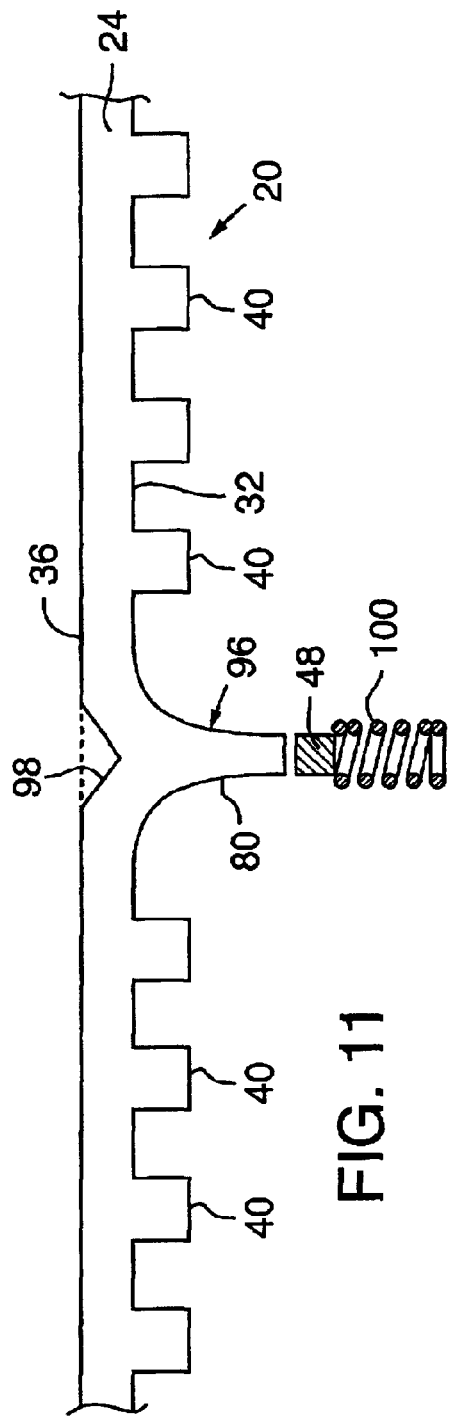
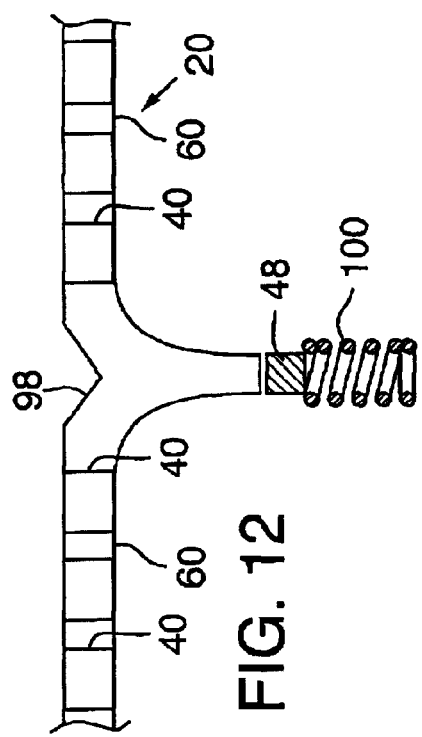

PHOTOACOUSTIC SPECTROSCOPY SAMPLE ARRAY VESSEL AND PHOTOACOUSTIC SPECTROSCOPY METHOD FOR USING THE SAME

This invention was made with Government support under Contract DE-AC0676RLO1830 awarded by the U.S. Department of Energy. The Government has certain rights in this invention.

FIELD OF THE INVENTION

The present invention relates to photoacoustic spectroscopic sample array vessels and photoacoustic spectroscopic analysis of samples held in such sample array vessels.

BACKGROUND

The science industry, and the bioscience and environmental industries in particular, rely on the analysis of large numbers of samples for various studies. The need for rapid turnaround time coupled with the high costs of labor and chemical waste disposal have resulted in the development of automated array-based techniques that analyze samples using optical spectroscopy. Although these conventional absorption-based techniques are applicable to a wide spectrum of analytes, they have low sensitivity.

The two major types of optical spectroscopy currently used in array-based analysis include absorption spectroscopy and fluorescence spectroscopy. The most common technique is conventional absorption spectroscopy. Light at a given wavelength is transmitted through the sample, and the decrease in intensity relative to the original beam is monitored. The concentration of absorbing substance is determined using the Beer-Lambert law, which requires knowledge of the intrinsic absorptivity of the substance, the path length of light through the sample, and the ratio of incident and transmitted light intensities. Because direct measurement of absorption involves sensing a small decrease in the strength of a high background signal (i.e., the intensity of the unblocked light beam), conventional absorption spectroscopy is a low signal-to-noise technique. As a consequence, it has limited sensitivity (typically on the order of $10^{-3}$ absorbance units, corresponding to absorption of about 0.2% of the incident light by the sample). This analysis method does, however, have wide applicability. A large number of analytes absorb light with sufficient efficiency to be detected by a decrease in transmissivity.

The other major type of spectroscopy in common use with sample arrays is fluorescence spectroscopy. This technique also relies on absorption of incident light by the sample, but detection is based on the emission of light of lower energy (longer wavelength) as the absorber decays from the excited state. The background signal of the detector, therefore, is zero (except for "dark current" noise in the electronic circuitry), and the signal-to-noise is very high.

The sensitivity of fluorescence depends not only on the absorptivity of the sample, but on the intensity of the incident light and the quantum yield of the conversion of absorbed energy to fluorescent light. Under optimal conditions, fluorescent samples can be measured at a sensitivity of about $10^4$ better than conventional absorbance spectroscopy. This sensitivity, however, is achieved at the cost of versatility. Few analytes fluoresce with the yield needed for wide application of the technique. Fluorescence spectroscopy is made practical for non-fluorescing analytes by tagging them with large (e.g., ca. 500 Dalton) fluorescent molecules, thus adding an additional costly step in the overall analysis and possibly altering the chemistry of the analyte in the process.

Although both conventional absorption spectroscopy and fluorescence spectroscopy rely on the absorption of light by the analyte, they differ significantly in their sensitivity and versatility. Absorption spectroscopy is easily applied to a wide variety of analytes, but has inherently poor sensitivity. Fluorescence spectroscopy is sensitive, but only for a limited number of molecules. An array-based analysis technique is needed that combines the strengths of these two spectroscopic approaches to yield both high sensitivity and wide applicability.

Photoacoustic spectroscopy (PAS) is based on the absorption of light energy by a molecule. The signal in PAS, however, is not detected by monitoring the transmittance or emission of light. Instead, in PAS, the signal is monitored by acoustic detection. Specifically, photoacoustic spectroscopy detection is based on the generation of acoustic waves as a consequence of light absorption. Absorption of light by a sample exposed thereto excites molecules in the sample to higher rotational/vibrational/electronic states. Return to the ground state releases the absorbed energy to the surrounding medium, either as light or heat. Collisions of the molecules transfer the rotational/vibrational energy to translational energy, i.e., heat. Modulation of the light intensity (turning the light on and off as the sample is exposed) causes the temperature of the sample to rise and fall periodically. The temperature variation of the sample is accompanied by a pressure variation that creates a sound wave (gas samples must be in a closed volume). The sound wave can be detected with a sensitive microphone.

Conventionally, a sample to be analyzed by photoacoustic spectroscopy is placed in a cuvette or other similar singular sample holder. Although obtaining the advantage of PAS analysis selectivity and sensitivity, the known single-sample analysis is slow and labor intensive. There is a need for development of sample array vessels including acoustic detectors operable with PAS systems for rapid analysis of multiple samples and methods for PAS sample analysis using the same.

SUMMARY

Presently disclosed is a photoacoustic spectroscopy (PAS) sample array vessel comprising a vessel body having multiple sample cells for holding solutions to be analyzed by photoacoustic spectroscopy. The sample array vessel further includes at least one acoustic detector acoustically coupled with the vessel body and capable of receiving an acoustic signal from at least one sample cell. The acoustic detector may comprise a transducer. Further disclosed is a method for PAS analysis of analytes in a solution. The method includes using a sample array vessel having a matrix of sample cells with solutions for analysis therein, exposing the solutions to a light beam to cause analytes in the solutions to emit acoustic signals, and detecting the acoustic signals generated by the analytes. The method may further comprise using a transducer to detect the acoustic signals generated by the analytes.

BRIEF DESCRIPTION OF THE DRAWINGS

FIG. 3b is a partial side view of the embodiment of the sample array vessel shown in FIG. 3a.

FIG. 5 is a partial bottom view of an embodiment of a PAS sample array vessel including directed acoustic fins connectable to one or more acoustic detectors.

FIG. 6 is a partial bottom view of an embodiment of a PAS sample array vessel including directed acoustic fins connectable to a collection bar connectable to one or more acoustic detectors.

FIG. 7 is a partial top view of an embodiment of a collection bar for a PAS sample array vessel (not shown).

FIG. 8 is a partial side view of an embodiment of an acoustic lens for a PAS sample array vessel (not shown).

FIG. 11 is a partial side view of an embodiment of a PAS sample array vessel showing a detachable acoustic detector.

FIG. 12 is a partial side view of an embodiment of a PAS sample array vessel showing a detachable acoustic detector.

DETAILED DESCRIPTION

Photoacoustic spectroscopy (PAS) sample array vessels and photoacoustic analysis methods are disclosed. The PAS sample array vessels and methods provide for rapid sequential or simultaneous PAS measurement of multiple samples, in various arrays, e.g., in an n, m matrix. The PAS methods and sample array vessels may be used to analyze gas, liquid, and solid samples for any type of species capable of absorbing incident electromagnetic energy. For example, the sample arrays and PAS analysis methods disclosed herein may be used to speciate various organic and inorganic transition, actinide, and lanthanide metals in solution, biomass fermentation, DNA and RNA, bacteria, to monitor serum glucose levels, and to detect pH and $CO_2$, oil in water, water in oil, hydrogen gas, components of a gas headspace, non-destructive measurement of Cr(VI), and various species dissolved in a glass matrix.

Figure 1:
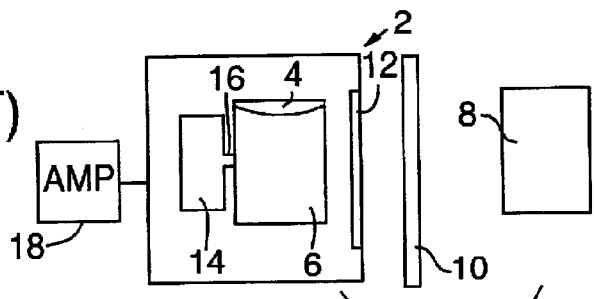
FIG. 1 shows a conventional photoacoustic spectroscopy system.

With reference to FIG. 1, in conventional PAS apparatus 2 a single cuvette 4 holds a sample 6 for analysis. The sample 6 to be analyzed is irradiated intermittently by an excitation source 8, light of a selected wavelength. The light is emitted from the excitation source 8 and is optically directed to a light chopper 10, typically a slotted disk that rotates to effectively "switch" the light from the excitation source on and off. The intermittent light travels through optical filters 12 to deliver intermittent light of a selected wavelength. The light then enters the cuvette 4 containing the sample 6. As the sample 6 absorbs energy from the light, acoustic waves or signals are generated. An acoustic detector 14 detects acoustic signals. Typically, the conventional acoustic detector used is a microphone connected to the cuvette 4 directly or via an acoustic channel 16. An amplifier 18 is electrically connected to the acoustic detector 14 to receive and amplify electrical output from the acoustic detector 14.

The present PAS methods and sample arrays take advantage of the fact that the measurable physical parameter in PAS analysis is the acoustic signals generated by changes in pressure ($\Delta P$) due to absorption of electromagnetic energy. Thus, the unique properties of PAS absorption are amenable to relatively small sample volume analyses. Specifically, the amplitude of the PAS signal, directly proportional to the $\Delta P$, is dependent only on the density of the absorbed energy. In other words, the signal may be represented as:

$$\text{Signal} \sim \Delta P \sim (\beta/\alpha C_p \rho)(E_{abs}/V_o)$$

wherein $\Delta P$ is the pressure change in the sample, $\beta$, $\alpha$, $C_p$ and $\rho$ are the thermoelastic properties of the solution or matrix expansivity, compressibility, heat capacity, and density, respectively, $E_{abs}$ is the quantity of energy in joules absorbed by the sample and $V_o$ is the irradiated volume (the irradiated volume is either less than or equal to the volume of the sample). As the path length is reduced both the absorbed energy and the volume are reduced simultaneously. Thus, the signal remains constant.

Furthermore, $\Delta P$ is independent of the path length. Because $\Delta P$ is a measure of the change in force per unit area, the signal is independent of the size of the detector (as long as the detector has sufficient electrical capacitance, as detailed below). Accordingly, a reduction in both the sample volume and the acoustic detector area as disclosed provides for rapid, array-based sample analyses without a loss in analytical selectivity or sensitivity. The disclosed PAS methods for simultaneous or sequential multiple sample array PAS analyses and sample array vessel apparatus also provide as much as a thousand fold increase in detection sensitivity as compared to conventional, single sample cuvettes, without sacrifice as to applicability.

More particularly, the factors affecting amplitudes of PAS signals S(V), include:

1) the energy absorbed per unit excitation volume (i.e. sample volume), $$E_\lambda(1-10^{-A_\lambda})/V_o \qquad (1)$$

where $E_\lambda$ is the energy per light pulse (J), $A_\lambda$ the absorbance of the sample at the wavelength ($\lambda$) of the light pulse (dimensionless), and $V_o$ the irradiated volume (mL);

2) the thermo-elastic properties of the solution ("solvent") containing the analyte, $$\beta/\alpha C_p \rho \quad (2)$$

where $\beta$ is the thermal coefficient of expansion of the sample (° C.$^{-1}$), $\alpha$ is the isothermal compressibility of the sample (Pa$^{-1}$), $C_p$ is the molar heat capacity of the sample (J° C.$^{-1}$g$^{-1}$), and $\rho$ is the density of the sample (g mL$^{-1}$);

3) the acoustic geometry and transmissivity of the solvent (i.e., the solution containing an analyte of interest) and other materials used to form an acoustic bridge between the sample and a detector, e.g., a transducer, $$\left\{ \sum_{i=1}^{n} (r_{i-1}/r_i) \exp[k_i(r_{i-1}-r_i)][1-(z_i-z_{i+1})^2/(z_i+z_{i+1})^2] \right\} \quad (3)$$

where n is the number of distinct media "i" in the acoustic bridge (including piezoelectric material in a transducer), $r_i$ is the radial distance of the acoustic wave from the center of the excitation volume (m) ($r_0$ corresponds to the radius of the excitation volume), $k_i$ is the acoustic absorption coefficient for waves of known frequency and velocity in medium i (m$^{-1}$), and $Z_i$ is the acoustic impedance of medium "i" wherein medium i is an acoustically homogeneous medium through which sound passes en route from a source to a transducer (kg m$^{-2}$s$^{-1}$); and 4) the efficiency of the transducer that converts the acoustic impulse into an electric impulse, $$K_{tw} h(d_{tw}/\epsilon_0 \epsilon_n)(C_t/C_{circuit}) \quad (4)$$

where $K_{tw}$ is the electromechanical coupling coefficient for the specific orientation of transducer (t) and acoustic wave (w), h is the thickness of the transducer element in the direction of acoustic wave travel (m), $d_{tw}$ is the piezoelectric strain constant for the transducer/wave orientation (C N$^{-1}$), $\epsilon_0$ is the permittivity of a vacuum (C V$^{-1}$m$^{-1}$), $\epsilon_n$ is the relative dielectric constant of piezoelectric material in the transducer, and $C_t$ and $C_{circuit}$ are the respective capacitances of the transducer and the total circuit (transducer and cables) feeding into the amplifier (pF). $K_{tw}$ and $\epsilon_n$ are dimensionless.

Combination of the four factors outlined above provide the following equation for expression of the signal S, assuming a cylindrical excitation (sample) volume with radial detection of a single acoustic mode in the transducer:

$$S = [E_\lambda(1-10^{-A\lambda})/V_o][\beta/\alpha C_p \rho] \quad (5)$$

$$\left\{ \sum_{i=1}^{n} (r_{i-1}/r_i) \exp[k_i(r_{i-1}-r_i)][1-(z_i-z_{i+1})^2/(z_i+z_{i+1})^2] \right\}$$

$$[K_{tw} h(d_{tw}/\varepsilon_0 \varepsilon_n)(C_t/C_{circuit})]$$

PAS Sample Array Vessels

Figure 2:
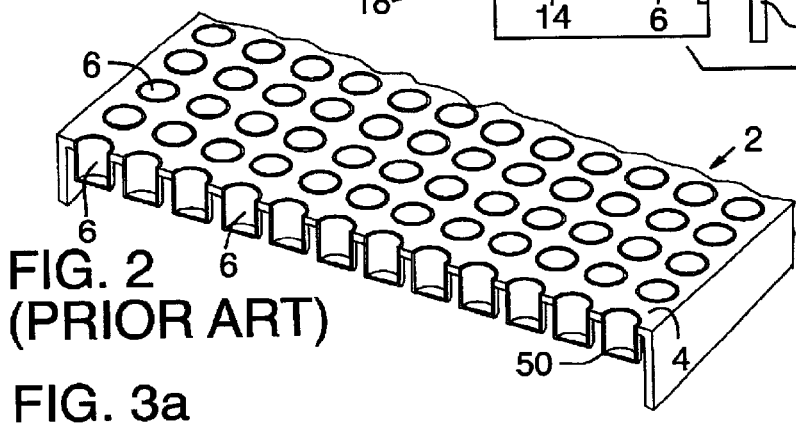
FIG. 2 is a perspective view of a conventional microtiter plate.

A conventional microtiter plate is shown in FIG. 2. Such a conventional microtiter plate 2 includes a body 4 having multiple sample wells 6. Conventional microtiter plates (such as microtiter plate 2) are commercially available from sources such as MicroLiter Analytical Supplies, Millipore, and Wheaton Science Products.

Figure 3A:
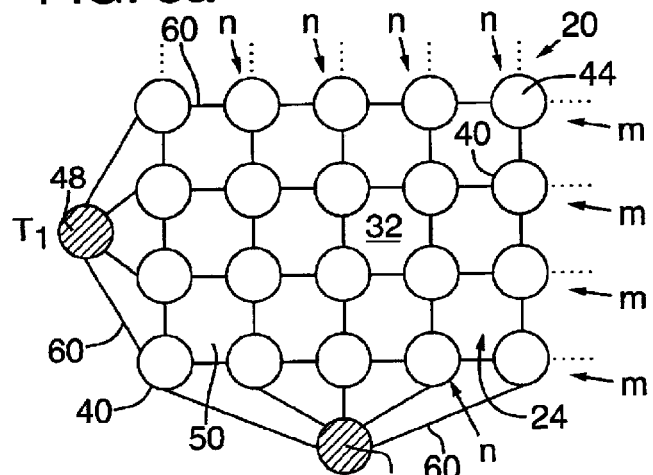
FIG. 3a is a partial bottom view of an embodiment of a PAS sample array vessel including acoustic fins connectable to one or more acoustic detectors.
Figure 3B:
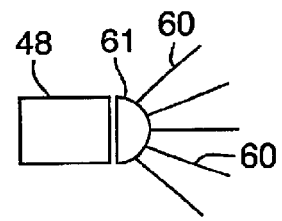

FIG. 3a is a top view of an embodiment of the sample array vessel 20 presently disclosed (FIG. 3b is a partial side view of the same embodiment). The sample array vessel 20 comprises a vessel body 24 comprising a plate with an upper surface 32 and a lower surface. Vessel body 24 further includes multiple sample cells 40 formed on or connected to the plate to form an arrangement or array of sample cells 40, e.g., an n, m matrix as shown in FIG. 3a. The vessel body 24 is formed of any sufficiently rigid material in which or to which sample cells 40 may be formed of or connected to, such that the sample cells are adequately supported by the vessel body. For example, the vessel body 24 may be formed of a plastic such as polyethylene or polypropylene.

The sample cells 40 may be any of a variety of shapes. For example, the sample cells may form hollow cylinders (having a bottom plate to hold samples therein) as shown in FIG. 3a. Each sample cell 40 comprises a well 44 for holding a sample to be analyzed. The sample cells 40 are formed of any sufficiently rigid material that is suitably transmissive to acoustic waves (e.g., a sufficiently hard material for suitable acoustic transmissibility but suitably soft so as to absorb acoustic signals generated by analytes in a sample within the sample cell 40). Good results are obtained with sample array vessels 20 having sample cells 40 formed of materials, such as polystyrene, polyethylene, and/or polypropylene.

To improve acoustic transmission in the sample array vessel 20 from sample cell 40 to sample cell 40, and through acoustic fins 60 (discussed below) to the acoustic detector, space or air gaps 50 (see, e.g., FIGS. 2 and 3) between the sample cells 40 are preferably filled with an acoustic transmissive material. Any material capable of effectively absorbing and transmitting acoustic waves may be used. For example, good results are obtained when gaps or spaces 50 between the sample cells 40 are filled with epoxy or silicon rubber.

Figure 14:
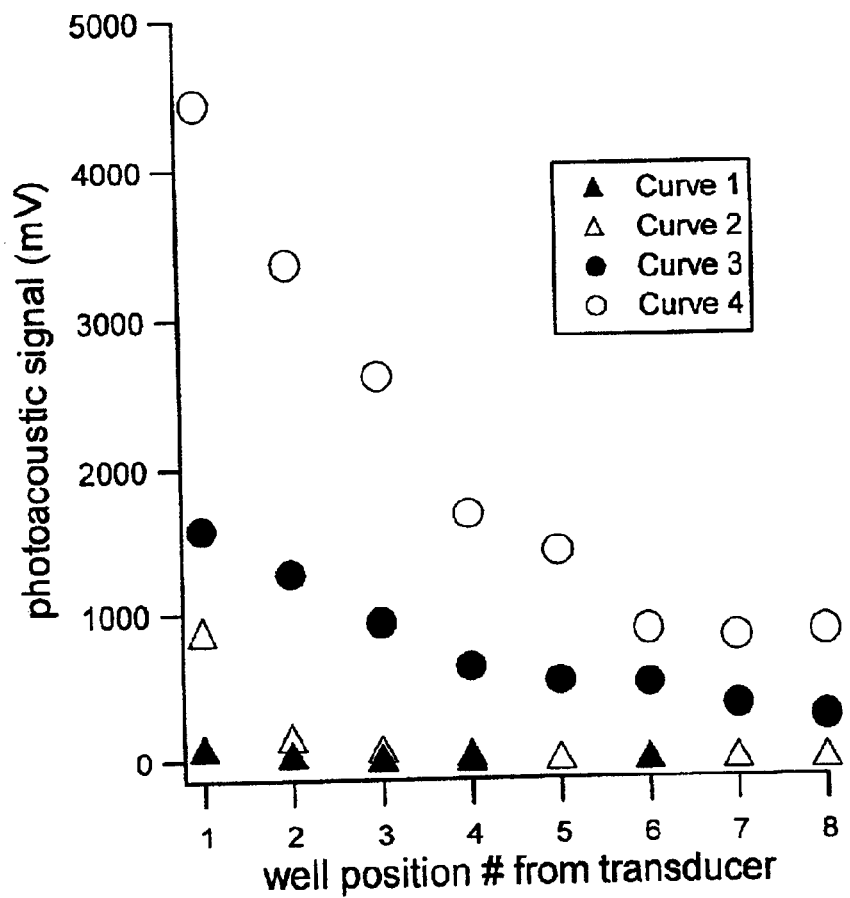
FIG. 14 shows acoustic sensitivities of sample array vessels including differing gap-filling material.

FIG. 14 illustrates the improved acoustic transmissivity and, hence, increased acoustic signal sensitivity for sample array vessels 20 including acoustic gap-filling material in the gaps 50 between sample cells 40. Specifically, a sample array vessel 20 having no acoustic gap-filling material has relatively low acoustic sensitivity as illustrated by curve 1 in FIG. 14. A sample array vessel having silicon formed in the gaps between the sample cells 40 shows improved acoustic transmissivity (see curve 2 in FIG. 14) and, hence, acoustic signal sensitivity for sample cells positioned nearer the acoustic detector. A sample array vessel 20 having an epoxy formed in gaps between the sample cells 40 has improved acoustic transmissivity and, hence, acoustic signal sensitivity for all sample cells in the array vessel. The epoxy may comprise, for example, a quick-setting epoxy (available from, e.g., Radioshack epoxy #64-231313, see curve 3 in FIG. 14) and/or a regular setting epoxy (available from, e.g., Dexter Corp, of Olean, N.Y., epoxy RE2038/HD3404, see curve 4 in FIG. 14). Those sample cells positioned closest to the acoustic detector (e.g., well 1) showed the highest level of acoustic sensitivity. A sample array vessel 20 having epoxy RE2038/HD3404 filling gaps between sample cells 40 improves acoustic transmission from all of the sample cells in the vessel and shows significantly improved acoustic transmission from sample cells positioned nearest an acoustic detector. Such a sample array vessel provides significantly increased acoustic signal sensitivity (see curve 4 in FIG. 14).

Arrangement of the sample cells 40 of the sample array vessel 20 may take any of a variety of forms. For example, a sample array vessel may have cells arranged in an n, m matrix, wherein n and m are integers from 1 to as large as can be reasonably handled by operators and PAS apparatus. Sample array vessels having about 24, 96, 384, 864, or 1536 sample cells with a 2:3 row-to-column ratio provide good results. It is understood, however, that either n or m of the matrix may be larger or smaller than the recited values, depending upon sample cell size, detector size, and arrangement.

The embodiment of the sample array vessel 20 shown in FIG. 3a, as well as the alternative embodiments discussed below, may include a single or multiple acoustic detectors 48. The acoustic detectors 48 may comprise any suitable acoustic detector, such as microphones or transducers (e.g., piezoelectric transducers). Suitable ceramic-type transducers are available from a number of commercial sources such as PAC, Material Systems Inc., Panametrics, PCB, Stavely, or KKB. Additionally, piezoelectric crystals available from manufacturers such as Channel Industries, Sensor Technology Ltd., and Valpey Fisher or flexible polymeric transducers, such as polyvinylidenefluoride (PVDF) (commercially available from Ktech Corporation, of Albuquerque, N. Mex.) may be used. Immersion detectors (discussed below) comprising, e.g., thin probes such as VP-A50 probes available from Valpey Fisher may also be used in particular embodiments of the sample array vessels. Although acoustic detectors may be referred to at times herein as "transducers" it is to be understood that any suitable acoustic detector may be utilized.

Embodiments utilizing arrays of acoustic detectors 48 may require use of relatively small transducers. The transducer, however, must have sufficient capacitance, which decreases with the contact area of the transducer. Low capacitance means low ability to drive a signal through circuitry connecting the transducer to an amplifier. To maximize voltage from a transducer, contribution to $C_{circuit}$ (i.e., the associated cables and connectors of the electronic circuitry) is preferably minimized.

Of the embodiments of the sample array vessels that include one or more acoustic detectors, the acoustic detectors may be connected to or arranged relative to the sample cells 40 in a variety of manners. For example, to receive acoustic signals from each of the sample cells 40, acoustic detectors 48 may be connected to or arranged relative to the sample cells 40 by a variety of acoustic bridges. The detectors may be positioned to receive acoustic signals from the sample cells by direct contact (e.g., contact transducers), air coupling (e.g., air-coupled transducers) or by immersion (e.g., immersion transducers FIGS. 15a–15c).

Figure 15A:
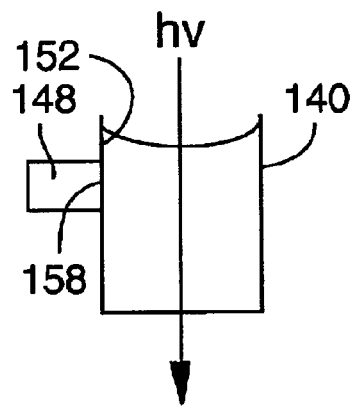
FIGS. 15a–15c show alternative acoustic bridge arrangements for embodiments of sample array vessels including one or more acoustic detectors.

With reference to FIG. 15a, an acoustic bridge between each sample cell 140 and an associated detector 148 may comprise a contact bridge 158. The contact bridge 158 is formed between a wall 152 of the sample cell 140 and the detector 148. An acoustic coupling fluid (e.g., grease, water, epoxy) may be placed at the contact bridge 158 between the detector 148 and an outer surface of the wall 152 of the sample cell 140. A contact-detector arrangement preferably utilizes a transducer 148 in direct physical contact with the wall 152 of the sample cell 140. Piezoelectric transducers having resonant frequencies of from about 100 KHz to about 10 MHz have been found to be especially useful.

With a direct contact design, a contact detector 148 (FIG. 15a), e.g., a contact transducer, preferably contacts or encapsulates at least a portion of the sample cell 140. For example, the detector may comprise a hollow cylindrical transducer that fits about the outside of the wall of a sample cell 40 of the sample array vessel 20 (see, e.g., FIGS. 9 and 10). Alternatively, the detectors may comprise flexible polymeric transducers, such as PVDF transducers that may encompass a portion of the inside or outside wall of a sample cell or otherwise contact the sample cell or an acoustic collector post (as discussed below). Flexible detectors may accommodate slight stress differences arising from variations in sample cell geometry. A hollow-type ceramic transducer filled with a flexible, acoustically transmissive material, such as a plastic liner, may be used to minimize mechanical stress on the transducer as it fits about the outside wall of the sample cell. Although sample cells of the sample array vessel 20 are generally discussed herein as being cylindrical in shape, the sample cell may be of any acoustically suitable shape.

Figure 15B:
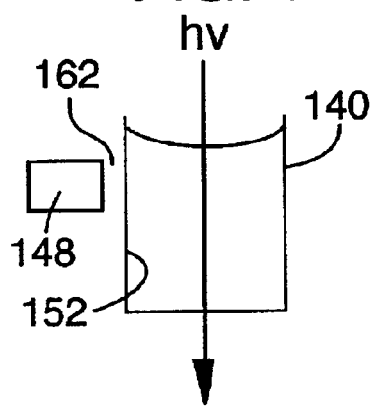

Although many embodiments of the sample array vessels primarily are discussed and illustrated utilizing contact acoustic detectors, such as contact transducers, any suitable acoustic detector may be used with any of the embodiments of the sample array vessel. That is, any suitable acoustic bridge between the sample array vessels and acoustic detectors may be used (including but not limited to air coupling and immersion coupling). For example, the sample array vessel 20 may include an air-coupling acoustic bridge 162, wherein the acoustic bridge comprises air between an outer surface of a wall 152 of a sample cell 140 and an associated detector 148 (FIG. 15b). Detectors 148 that are air-coupled to the sample cell 140 may avoid problems associated with reproducible contact (i.e., reproducible force on the detector at the time of contact) through ensuring reproducible distance and orientation relative to the sample cell to be analyzed. Preferably, the transducer 148 is air-coupled near the sample cell 140. An acoustic channel (e.g., 104 in FIG. 17) may be included to air couple the detector to the sample cell.

Figure 17:
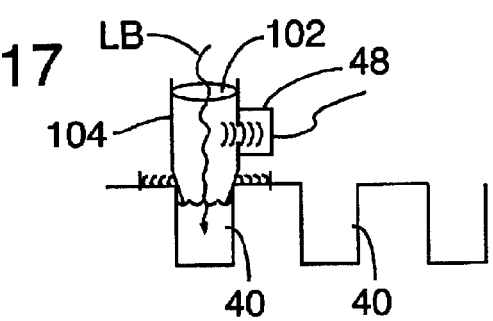
FIG. 17 shows an embodiment of a sample array vessel with an air-coupled acoustic detection system.

An illustrative embodiment of an air-coupled detection system is shown in FIG. 17, wherein a single-cell, air-coupled detection system comprises an optical window 102, an acoustic detector 48, and an air-column 104. The detector 48 may be mounted to a side portion of the air column 104 as shown or may take any of a variety of acoustically suitable positions on the air-coupled detection system. The air-coupled detection system is positioned above a sample cell 40 such that a light source LB may be directed through the optical window 102 and into the sample cell. Any suitable sealing means, such as a non-sticking rubber gasket (not shown) may be positioned between the sample cell 40 of the sample array vessel and the portion of the air column 104 that contacts the sample array vessel surface, to ensure a suitable seal therebetween. Sealing the sample cell 40 to be analyzed aids in the transmission of acoustic waves from the sample cell 40, through the air column 104 and to the detector 48.

Such an air-coupled detection system may be moved from sample cell to sample cell of a sample array vessel (or the air-coupled detection system may be stationary and the sample array vessel may be moved to place the sample cells to be tested in contact with the air-coupled detection system). An air-coupled detection system (such as the embodiment shown in FIG. 17) may avoid the contamination difficulties sometimes encountered with immersion-detection systems and difficulties associated with reproducible contact sometimes encountered with contact-detection systems.

The placement of air-coupled detector embodiments relative to sample cells of a sample array vessel may be the same as or similar to that discussed below relative to contact acoustic detector placements. For example, an air-coupled detector may be fixed at each sample cell 40, there may be a single or a few air-coupled detectors fixed strategically about the sample array vessel 20 or there may be one or more movable air-coupling detectors positionable to detect acoustic signals from sample cells 40 in the sample array vessel.

Figure 15C:
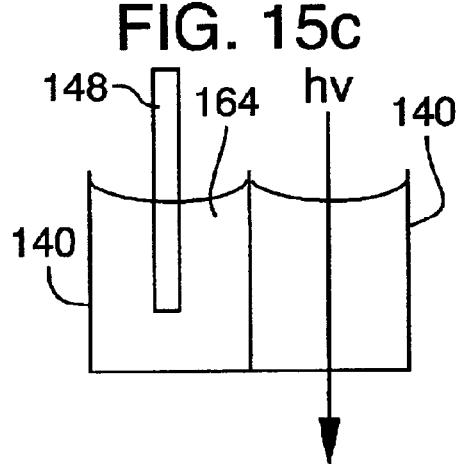

The sample array vessel 20 may alternatively have a liquid-coupling acoustic bridge, wherein an acoustic detector 148 is immersed in a liquid in a sample cell adjacent or near a sample cell 140 to be analyzed (FIG. 15c). For immersion detection, the acoustic detector preferably comprises a thin probe, such as a VP-A50 probe (available from Valpey Fisher) of a suitable size to fit within sample cell volumes of the sample array vessel 20. The immersion detector may be movable such that it can be moved and placed in a sample cell immediately adjacent the sample cell to be analyzed to avoid cross contamination between samples. With such an arrangement, at least one sample cell in the sample array vessel would be sacrificed for the initial measurement of a first sample cell of the sample array vessel. Thereafter, the immersion detector would be moved and immersed in the sample cell just previously measured for analysis of the next, immediately adjacent sample cell. In situations where cross contamination is not a concern, or the immersion detector can be cleaned between samples, it can be placed directly into the cell being analyzed.

Similar to the arrangement discussed below relative to contact acoustic detectors, the sample array vessel may include an immersion detector, wherein one sample cell per row of sample cells is sacrificed and the immersion detector is positioned only in the first sample cell of the row and detects acoustic signals from all of the sample cells in the row. Alternatively, a single immersion detector may be positioned in a sample cell centrally located within the sample array vessel or about a group of sample cells within the sample array vessel. Such a sample array vessel provides a mechanically simple device as compared to a sample array vessel including the use of a movable detector.

Another type of immersion detector that may be used with the sample array vessel of the present invention may comprise an immersion transducer formed to fit within the sample cell to fit near or to contact interior walls of the sample well. For example, an array vessel having cylindrically shaped sample cells may include a hollow cylinder detector formed of a material such as PVDF or a ceramic piezoelectric that is insertable into the cylindrically shaped well. Such an arrangement avoids some impedance loss associated with a strictly aqueous acoustic contact. Further, the use of the sample fluid within the sample cell minimizes friction during transducer placement.

One or more acoustic detectors may be placed relative to the sample array vessels in any acoustically suitable position. The acoustic detectors may be attached to the sample array vessel or may be a part of a PAS system. With acoustic detectors affixed to a PAS system, the detectors may be acoustically connected to ("docked in") the sample array vessel when the vessel is positioned within the PAS system. Whether affixed to the sample array vessel or part of a PAS system and acoustically connected to the vessel when placed in the PAS system, the acoustic detectors may be positioned in a variety of locations in or relative to the sample array vessels. The following embodiments illustrate a few of a variety of acoustic detector placements. The sample array vessels are not limited to such embodiments discussed and/or illustrated in the accompanying figures but include acoustic detectors in any of the variety of acoustically suitable detector placements.

For example, as shown in FIGS. 3a and 3b, the sample array vessel 20 may include one or more acoustic detectors 48, positioned about the perimeter of the vessel to analyze all of the sample cells 40 in the sample array vessel 20. As shown in FIG. 3a, a first acoustic detector T1 (or more) may be positioned at the end of rows m and a second acoustic detector T2 (or more) may be positioned at the end of rows n (when the sample cells are arranged in a matrix). As shown, the acoustic detectors 48 may be connected to one or more rows of sample cells 40 of the sample array vessels 20.

The specific embodiment illustrated in FIG. 3a includes at least two detectors T1 and T2, each of which are acoustically connected to all of the sample cells 40 in the sample array vessel 20. Thus, acoustic signals generated by analytes contained in the sample cells 40 would be detected by at least two detectors (i.e., T1 and T2). The fewer the acoustic detectors per sample array vessel, the fewer calibration steps needed for PAS analysis of samples within the sample array vessel.

The acoustic detectors 48 in the FIGS. 3a and 3b embodiment are preferably acoustically connected to each of the sample cells 40 by acoustic fins 60. For the matrix sample cell arrangement shown in FIG. 3a, acoustic fins 60 are shown to extend both vertically and horizontally within the sample cell matrix. Acoustic fins 60 preferably connect each sample cell 40 to the next sample cell 40 and eventually lead to the one or more acoustic detectors 48. The acoustic fins 60 may connect from one sample cell 40 to the next sample cell 40 by a single contact with each cell (e.g., contact with a wall of the sample cell 40) or may wrap about a portion of the sample cell 40 wall and then lead to the next adjacent sample cell 40. The acoustic fins 60 may extend the full height of the acoustic cell 40 wall.

The acoustic fins 60 may be formed of any sufficiently rigid material that is suitably transmissive to acoustic waves. The acoustic fin 60 material is preferably sufficiently hard to effectively transmit acoustic waves but suitably soft so as to absorb acoustic waves generated by analytes in a sample within the sample cell 40. For example, acoustic fins 60 may be formed of a variety of different materials, such as polystyrene, polyethylene, polypropylene, plastics with mineral or metallic fillers (e.g., composite plastics), laminated carbon materials, metallic materials, and mixtures thereof In alternative embodiments of the sample array vessel, the acoustic fins 60 perform the dual function of forming the gap 50 filling material discussed above as well as acting as acoustic wave paths from the sample cells to the acoustic detector(s). Gap filling material may be used in conjunction with sample array vessels having acoustic fins 60 to increase acoustic sensitivity of the device.

When utilizing acoustic detectors 48 comprising, e.g., piezoelectric transducers cylindrical in shape with a sample array vessel as shown in FIGS. 3a and 3b, a substantially flat surface or end of the cylindrically-shaped transducer is (typically) the portion of the transducer that receives the acoustic signals. The transducer is, thus, preferably positioned such that the end or flat surface of the cylinder is substantially perpendicular relative to the direction in which the acoustic waves will travel.

Figure 4:
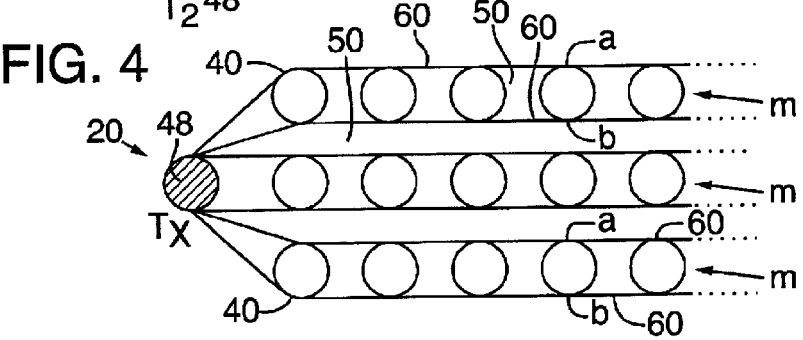
FIG. 4 is a partial bottom view of an embodiment of a PAS sample array vessel including acoustic fins connectable to one or more acoustic detectors.

In another embodiment, as shown in FIG. 4, the sample array vessel 20 may include acoustic fins 60 forming lines along one or two sides a, b of the sample cells 40 in the sample array vessel. The acoustic fins 60 of the FIG. 4 embodiment preferably extend along each row m of sample cells 40 from a first end 52 to a second end (not shown). Although the embodiment of the sample array vessel 20 shown in FIG. 4 includes two acoustic fins 60 extending along either side of each row m of sample cells 40, a single acoustic fin 60 for each row of sample cells may be used. A single acoustic fin 60 for each row m of sample cells 40 may provide a "narrower" acoustic signal to the transducer, due to possible differences in travel distances when more than one acoustic fin is utilized. Embodiments of the sample array vessel 20 wherein acoustic fins 60 are connected from one sample cell to the next (and then to the acoustic detector) in a substantially straight line (i.e., forming a limited number of (or no) turns) may reduce acoustic wave reflection and loss of acoustic signal sensitivity.

The acoustic fins 60 contact each sample cell at, at least, a portion of the sample cell 40 wall. The acoustic fins 60 are preferably connected to one or more acoustic detectors 48 positioned at the end of a set of sample cell 40 rows. As with all embodiments of the sample array vessel, the acoustic detectors 48 of the sample array vessel 20 embodiment shown in FIG. 4 may be affixed to the sample array vessel 20 or may be part of the PAS system in which the sample array vessel 20 may be placed.

The embodiment shown in FIG. 5 illustrates a directed acoustic fin 60 design wherein an acoustic detector 48 is positioned centrally in the sample array vessel or centrally about a group of sample cells 40 of the sample array vessel 20. For example, as shown, an acoustic detector 48 may be centrally positioned about a group of 24 sample cells 40. Thus, a sample array vessel 20 having 96 sample cells may include four acoustic detectors. The acoustic fins 60 of the FIG. 5 embodiment extend from a first end 62 connected to a sample cell 40 wall to a second end 63 connected to the acoustic detector 48. The acoustic fins 60 are preferably positioned such that they do not touch one another. The acoustic detectors 48 used may comprise, for example, a transducer embedded within the sample array vessel (or insertable into the sample array vessel). A hollow cylindrically shaped radially active plane-wave transducer is preferably positioned within the sample array vessel 20 such that the end of the cylinder is substantially parallel to (i.e., the axis of the cylinder is perpendicular to) the plane defined by the lower surface 32 of the sample array vessel 20).

In yet another embodiment of the sample array vessel 20, as shown in FIG. 6, the vessel may include one or more detectors 48, comprising, e.g., contact transducers, positioned at a collection bar 64. The face of the collection bar 64 preferably is positioned substantially perpendicular to the lower surface 32 of the sample array vessel 20. The collection bar 64 may be formed of the same material as the acoustic fins 60 or a different but acoustically suitable material. Each sample cell 40 is acoustically connected to the collection bar 64 (and hence the acoustic detector 48) via separate acoustic fins 60 extending from each sample cell and terminating at the collection bar 64. The acoustic fins 60 preferably do not contact one another. The acoustic detector 48 may be connected to the collection bar 64, for example, using an acoustic coupling fluid and a tensioning device or support (not shown). The tension device or support maintains the acoustic detector against the collection bar 64 to enhance transmission of acoustic signals from the sample cells via the acoustic fins 60 and collection bar 64 to the detector. If a cylindrical acoustic detector 48 is used, the detector may be, for example, positioned such that the end of the cylindrical detector is substantially parallel to the face of the collection bar and perpendicular to the plane defined by the lower surface 32 of the sample array vessel 20.

An embodiment of the collection bar 64 of the FIG. 6 sample array vessel 20 is shown in FIG. 7. Acoustic fins 60 extending from the sample cells 40 (see FIG. 6) preferably terminate at the collection bar 64 with tapered ends 66. Further, the collection bar 64 preferably tapers where connected to the acoustic detector 48 to have a cross-sectional area substantially equal to the cross-sectional area of the acoustic detector connected thereto. The tapering focuses the acoustic signals from the collection bar 64 to the acoustic detector 48 and minimizes reflection of the signals.

With reference to FIG. 8, an acoustic collector lens 70 may be used rather than a collection bar 64 (FIGS. 6 and 7). The collector lens 70 focuses the acoustic signals received (via acoustic fins 60) from the sample cells 40 to an acoustic detector 48. As with the collection bar 64, the acoustic collector lens 70 is preferably formed of the same material as the acoustic fins 60 of the sample array vessel 20. The collector lens 70 may be a bulbous shape or other acoustically suitable shape that focuses acoustic waves, limits reflections, and decreases in size from a first end 71 to a second end 72. The second end 72 of the collector lens 70 preferably has a cross-sectional area substantially equal to the cross-sectional area of the acoustic detector 48 to be connected thereto. The curved surface of the collector lens 70 allows acoustic signals to be received from the acoustic fins 60 attached thereto with minimal reflection and orients the acoustic waves received via the acoustic fins 60 toward the acoustic detector 48. The acoustic signal focusing of the collector lens 70 embodiment increases acoustic signal sensitivity of a sample array vessel 20.

Preferably, a sample array vessel 20 including a collector lens 70 also includes acoustic fins that have a first tapered end 64 connected to the collector lens 70 and a second tapered end 68 connected to a sample cell 40. Preferably, the second tapered end 68 of the acoustic fins 60 wrap about a portion of the sample cell 40 to increase the amount of acoustic signal the acoustic fin 60 absorbs from the sample cell. Preferably, the second tapered end 68 of the acoustic fins 60 encircle about one half of the sample cell exterior to minimize acoustic signal loss through reflection. The second end 68 of the acoustic fins 60 may taper down from its initial contact point with the sample cell 40 to be relatively thin at about half way around the sample cell wall to further minimize back-reflection of the acoustic signal.

Figure 9:
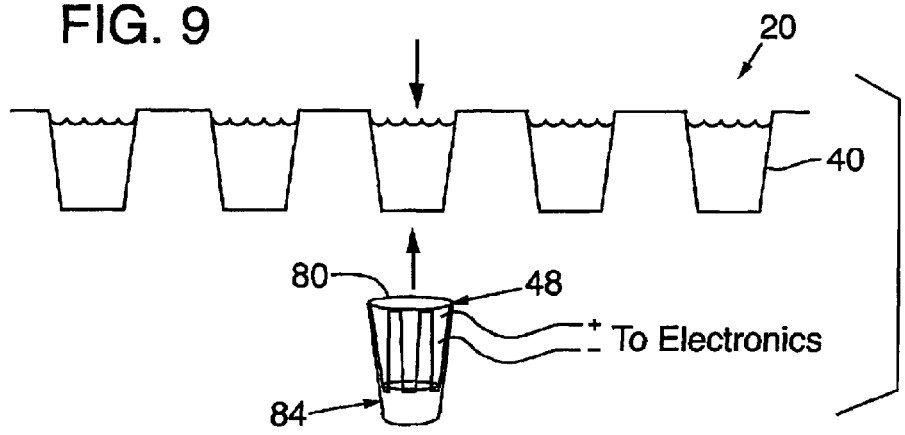
FIG. 9 is a partial side view of an embodiment of a PAS sample array vessel showing a detachable acoustic detector.
Figure 10:
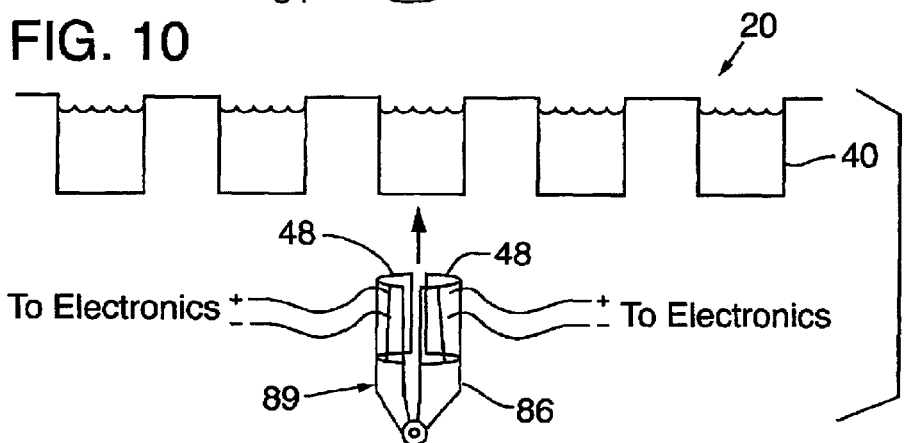
FIG. 10 is a partial side view of an embodiment of a PAS sample array vessel showing a detachable acoustic detector.

FIGS. 9 and 10 are cross-sectional views of embodiments of the sample array vessel 20. These embodiments of the vessel 20 include acoustic detectors 48 that contact each sample cell 40 from below. The acoustic detectors 48 may be moved from sample cell 40 to sample cell 40 to contact each sample cell. Alternatively, the detectors 48 may be affixed to a PAS system (not shown) and the sample array vessel 20 may be moved to connect each sample cell 40 with the detector sequentially.

The acoustic detector 48 used with the sample array vessel 20 of FIG. 9 may comprise, for example, a PVDF polymeric transducer. A more flexible detector minimizes problems encountered with differing cell geometries and typically has a higher sensitivity to pressure to provide more sensitivity to acoustic signal detection as compared to ceramic type detectors. In addition, the sample cells 40 of the sample array vessel 20 may be tapered as shown in FIG. 9 such that the sample cells gradually increase in diameter from the lower portion of the sample cells to the upper portions of the cells.

The PVDF transducer may comprise, e.g., a ring 80 of PDVF material bounded by a flexible support 84. The flexible support 84 may comprise, e.g., a slotted flexible support 84 bounding and supporting the acoustic detector 48 as shown in FIG. 9. The flexible support 84 may, however, comprise any of a variety of mechanical support devices as known to persons skilled in the art. The flexible support 84 ensures sufficient contact between the acoustic detector 48 (e.g., ring 80) and the sample cell 40 as the detector or the sample array vessel 20 are moved for sequential testing of each sample cell 40. As the detector 48 makes contact with the sample cell 40 the ring 80 slips about the outside wall of the sample cell 40. The acoustic detector 48 may alternatively comprise, e.g., a ceramic cylindrical piezoelectric transducer. To protect the ceramic transducer a wear coat, e.g., a plastic liner or the like, may be placed within the detector to protect the ceramic material from forces placed upon it when slipped about different sample cells. Although the FIG. 9 embodiment of the sample array vessel 20 shows only a single acoustic detector 48, there may be multiple acoustic detectors positioned to receive a like number of sample cells so that simultaneous analysis of the sample cells 40 in the sample array vessel may be performed.

Another possible embodiment of a detector system is shown in FIG. 10. As shown, the detector 48 may comprise two hemicylindrical ceramic transducers that are "clamped" about the sample cell 40 by a tensioning support 89. (Alternatively, a pair of PVDF transducers or transducers formed of other suitable materials may be used in this embodiment.) The tensioning support 89 as shown in FIG. 10 comprises a slotted clamping mechanism including a hinge 88. The tensioning support 89, when clamped or otherwise enclosed about the detector 48 supports the acoustic detector 48 and maintains contact between the detector and the sample cell. Again, the acoustic detector 48 is dimensioned to fit about and make contact with the outside wall of the sample cell 40. As with the FIG. 9 embodiment, the acoustic detector 48 and slotted tensioning support 89 may be affixed to a PAS system (not shown) and the sample array vessel 20 moved to analyze one or more sample cells (depending on the number of acoustic detectors present in the system). Alternatively, the acoustic detector 48 and slotted tensioning support 89 may be movable from sample cell 40 to sample cell 40. It is to be understood that the supports 84 and 89 may comprise any of a variety of suitable support mechanisms as would be known to those persons skilled in the art and are not limited to the designs shown in FIGS. 9 and/or 10.

As yet another alternative to the sample array vessel 20 embodiments shown in FIGS. 9 and 10, the acoustic detector 48 may instead be attached to a lower end of the flexible support 84 of FIG. 9 rather than comprising a ring or cylinder that fits about the sample cell 40. In such an embodiment, the flexible support 84 (or other suitable mechanism) would fit about the sample cell 40 of the sample array vessel and would act to transmit the acoustic signal from the sample cell 40 to the acoustic detector attached to the lower end of the support 84. Accordingly, the flexible support 84 would preferably be formed of a material similar to or the same as the material used to form the acoustic fins 60 of the sample array vessels discussed above. Such a device would not require the acoustic detector be of a shape and size that fits around or about the sample cell 40.

Figure 13:
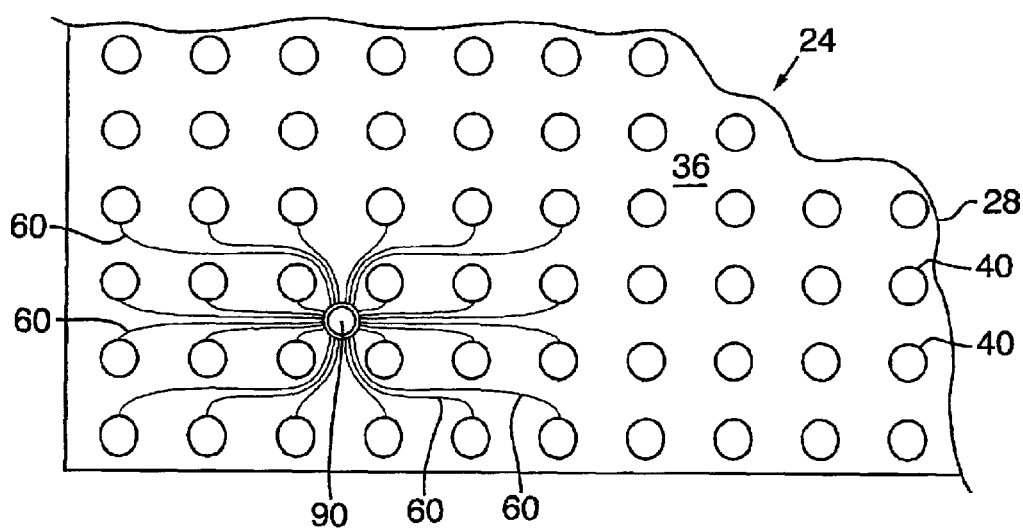
FIG. 13 is a partial top view of an embodiment of a PAS sample array vessel with a post collector connectable to an acoustic detector.

With reference to FIG. 13, in yet another embodiment of the sample array vessel 20, a post collector 90 is positioned centrally in the sample array vessel or about a group of sample cells 40. (Alternatively, the post collector may be otherwise positioned on the sample array vessel.) Acoustic fins 60 lead from each sample cell 40 in the group of sample cells to the post collector 90. Post collector 90 may comprise a docking station for an acoustic detector (not shown). For example, the collector post 90 may comprise a solid post or support that an acoustic detector contacts by, e.g., encapsulating a portion of an upper end of the collector post 90 (similar to the matter in which detectors may surround sample cells in the vessel shown in FIG. 9). Alternatively, an acoustic detector may simply contact an end portion of the post collector 90.

In another embodiment, the post collector 90 comprises a docking station such as a hollow cylinder for receiving an acoustic detector therein. The sample array vessel 20 shown in FIG. 13 shows only a single post collector 90 but may comprise multiple post collectors 90 positioned strategically about the array of sample cells 40. The sample array vessel 20 of FIG. 13 can provide for sequential or simultaneous PAS analysis of groups of sample cells or of all of the sample cells in the vessel; depending upon the number of detectors included, simultaneous sampling may require that each sample cell have a different acoustic travel distance from the sample cell to the corresponding detector.

Another embodiment of the sample array vessel 20 is illustrated in FIG. 11. The sample array vessel 20 includes a reflection collector bar 96. The reflection collector bar 96 preferably forms a tapered post 80 extending substantially perpendicular to the lower surface 32 of the vessel body 24, downward past the sample cells 40. The reflection collector bar 96 may be formed as part of the body 24 (i.e., be integral with the vessel body) or may be connected to the body. The reflection collector bar 96 may include a divot 98 to reflect and direct acoustic waves from the sample cells 40 down the tapered post 80 of the reflection collector bar 96. The divot 98 is preferably formed into the reflection collector bar 96 at an angle of about 45° relative to the upper surface 36 of the sample array vessel 20. An acoustic detector 48 (e.g., a piezoelectric transducer) may then be placed in contact with the reflection collector bar 96 and held in place by a support device, such as a spring 100.

Another embodiment of the sample array vessel 20 is illustrated in FIG. 12. This embodiment of the sample array vessel 20 is similar to that shown in FIG. 11 with the exception that acoustic fins 60 are included to run along the side of the sample cell 40 walls (similar, for example, to the acoustic fins 60 as shown in FIGS. 5, 6, 8, and 13) and to the reflection collector bar 96. As mentioned in relation to other embodiments, the reflection collection bar (and divot) may be positioned on an end edge of the sample array vessel or any other position on the sample array vessel such that the reflection collection bar suitably receives acoustic signals from the sample cells.

Figure 16:
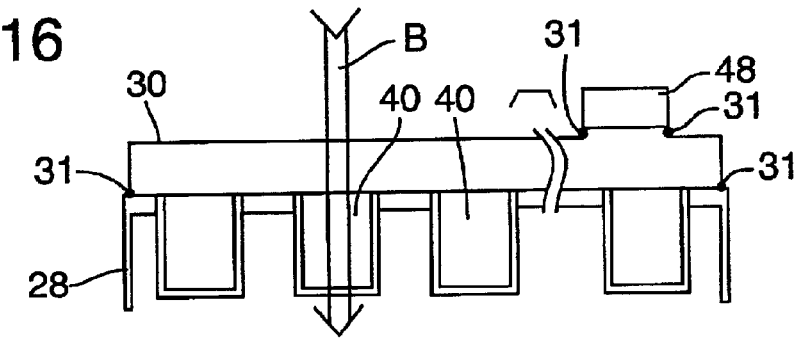
FIG. 16 shows an embodiment of a sample array vessel having an air-coupled acoustic detection system and a sealing plate.

Another embodiment of the sample array vessel includes a vessel having a sealing means, such as a cover plate to seal the sample cells of the vessel. For example, as shown in FIG. 16, a sealing plate 30 comprises a material transmissive to the desired incident light beam B. The sealing plate 30 preferably includes any suitable means 31 to ensure a substantially airtight seal between the sample array vessel body 28 and the plate 30 and between the plate 30 and an air-coupled acoustic detector 48 (or an acoustic-air channel as shown in FIG. 17). For example, rubber gaskets or seals formed of materials such as TEFLON, KALREZ, copper, VITON, and epoxy may be used. With such a sample array vessel, as the sample is exposed to the light source, the total gas volume in the sample cell expands against the detector providing increased sensitivity. If the sealed sample array vessel were to be further filled or compressed with a gas, e.g., helium, the acoustic sensitivity provided by the sample array vessel may be further increased.

Figure 18:
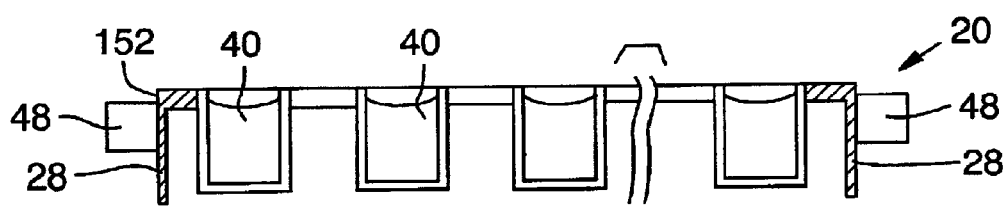
FIG. 18 is a side view of an embodiment of a sample array vessel including one or more side-mount acoustic detectors.
Figure 20:
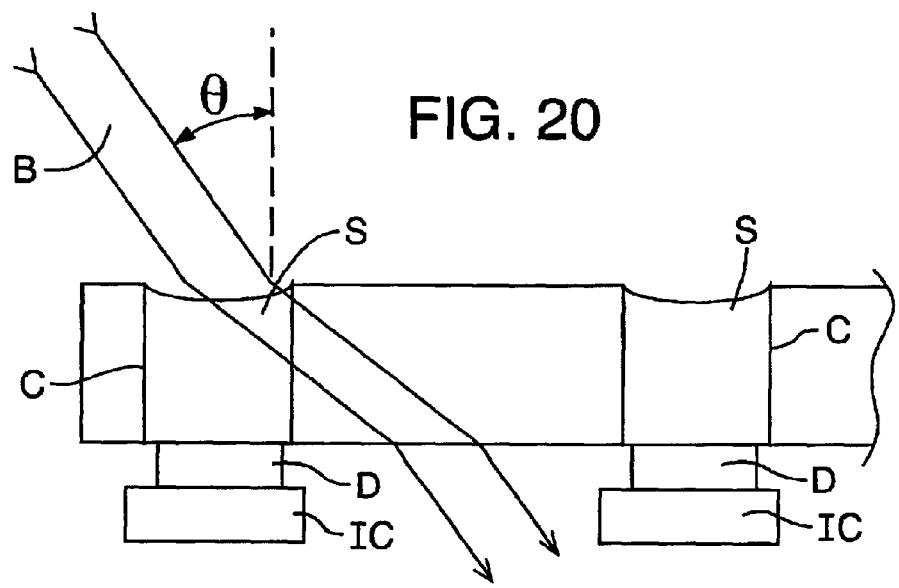
FIG. 20 shows a portion of an embodiment of a sample array comprising a refractive array, each sample cell including a detector positioned thereunder.

In another embodiment of the sample array vessel 20 (as shown in FIG. 18), the sample array vessel may simply include one to more acoustic detectors 48 positioned by or attached to one or more edges of the vessel body 28. Alternatively, as shown in FIG. 20, an acoustic detector D may be positioned beneath the sample cell C of the sample array vessel. There may be an acoustic detector D positioned beneath each sample cell to be tested or either of the sample array vessel or the detector may be moved to analyze each sample cell. Further, the detectors may be affixed to the sample array vessel itself or may be affixed to the PAS system (not shown) upon which the sample array vessel is aligned such that one or more detectors are positioned beneath the sample cells C. In addition, the detectors D may include integrated circuitry IC to transmit the signal received by the detector to a PC (not shown).

Figure 19:
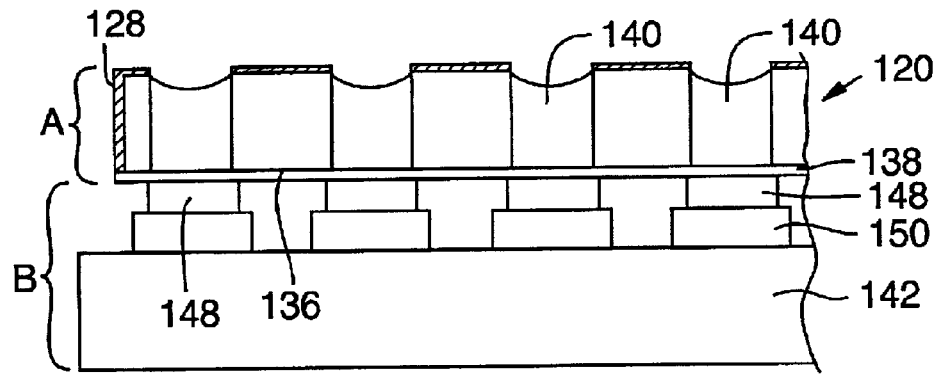
FIG. 19 is a side view of an embodiment of a sample array vessel including an acoustic detector positioned at each sample cell and a reflective plate.

As shown in FIG. 19, the sample array vessel 20 may further include a reflective layer or plate 38 positioned beneath the sample cells 40. The reflective layer or plate 38 may be connected to or connectable to the body 28 of the array or may simply be formed on or connected to the lower surfaces of the sample cells 40. The reflective plate 38 may comprise any material capable of reflecting the light source or irradiation directed from a radiation source in a PAS system into samples retained within the sample cells 40 without significantly impeding the transfer of an acoustic signal from the sample cells 40 to one or more acoustic detectors 48. For example, the reflective coating or plate 38 may comprise a metal, such as aluminum, gold, or may comprise a mirror.

As shown in FIG. 19 (and the FIG. 20 embodiment) the sample array vessel 20 may include a detector 48 positioned beneath each sample cell 40. Further, integrated circuitry 50 may be attached to or connectable to each detector 48. A base plate 42 may be included to support the integrated circuitry 50, and optionally the detectors 48 and the reflective plate 38. The sample array vessel 20 shown in FIG. 19 may be one complete unit or may form two or more separable units A, B. For example, the sample array vessel 20 may comprise unit A including the vessel body 28, sample cells 40 and reflective plate 38, and unit B including a base plate 42 with integrated circuitry 50 and detectors 48 (unit B rather than unit A may include the reflective plate 38). Unit B may be an integral part of the sample array vessel, may comprise a separable component of the array vessel or may be affixed to a PAS system whereupon the sample array vessel is aligned.

Embodiments of the sample array vessels 20 including acoustic detectors may further include one or more electrical interconnects (e.g., integrated circuits 50) extending from the detectors 48 to electrically couple the detector with circuitry (not shown) for processing and/or displaying signals generated by the detector. Each detector may be electrically coupled to one or more amplifiers (not shown) for amplifying signals generated by the acoustic detector.

PAS Analyses Methods

With conventional PAS sample analysis, the light source is typically modulated and monochromatized prior to reaching the sample. Modulation may be provided by mechanically chopping the light beam from a continuous source or using a pulsed source. For broadband sources, use of notch filters or reflectors achieve monochromatization. For bright sources of highly absorbing samples, grating monochromators may be used. The amplitude modulation needed for Fourier-transform PAS is obtained either by scanning continuously at an optimal mirror speed or in a step-scanning mode by dithering a mirror in an interferometer during data collection.

Conventional light sources for PAS are either limited in terms of wavelength selectivity (e.g., lasers) or pulse energy (e.g., flash lamps). The pulse energy needed for adequate sensitivity for the present invention PAS methods depends upon the absorptivity of the sample to be analyzed and the efficiency of the PAS apparatus. The presently disclosed PAS methods may include use of a flash-lamp source suitable to provide a sufficient amount of energy for discrete wavelength applications. For example, the flash-lamp source may comprise a SQ xenon flash lamp available from Hamamatsu. Wavelength selectivity with minimal loss in pulse energy may be achieved with a flash-lamp source using narrow-band filters or reflectors for a limited number of wavelengths (as described in Autrey et al., Tunable UV Visible Photoacoustic Detection, *Anal. Chem. Acta*, (2001), which is incorporated herein by reference).

For the disclosed PAS methods, when using variable pulse photoacoustic excitation sources, preferably sufficient energy densities are deposited in the sample to yield transient pressure changes of about $\geqq 1$ mPa. Further, preferably, there is a ratio of transducer frequency ($s^{-1}$) to source pulse width(s) of about $\geqq 5$. Preferably, the light source (or excitation source) has a pulse width of <5 $\mu$s and more preferably, 2 $\mu$s with pulse energy of greater than about 3 to about 30 $\mu$J. Pulse-laser sources may also be used to practice the methods. The wavelength of the light is preferably chosen based upon where the species of interest has the greatest absorbance and the sample cell material has the least absorbance, as known to those persons skilled in the art.

A notch filter may be used to provide narrow-band light. Additionally, fiber optics and reflective mirrors may be utilized to direct a light beam from the light source to a sample cell. Because the intensity of the light source decreases with increasing distance from the source, however, optical mirrors mounted on the sample array may require a standardization method (as known to those persons skilled in the art) to normalize for changes in light intensity for each sample cells in the sample array vessel. Preferably, optics to collimate the light focus on a fiber bundle, and to deliver the light beam to each sample cell in the sample array aid in the delivery of a constant path length for travel of the light beam. The light exiting such a fiber bundle is preferably shaped to provide an optimized energy density for each sample cell in the sample array vessel.

When using commercially available piezoelectric transducers for acoustic detectors, transient pressure changes in the order of 1 Pa can be detected with no electronic amplification of transducer signals. The use of low noise, high gain (e.g., 100–1000 gain) amplifiers available from Panametrics with the present methods permits the measure of mPa pressure changes with adequate signal averaging to reduce white noise. Analysis of equation (1) discussed above, showed that the photo-induced pressure change in the excitation volume (the sample volume to be analyzed) is equal to the product of the first two terms representing the density of the absorbed energy and the thermo-elastic properties of the solvent (i.e., term (1) absorbed incident light intensity per irradiated volume, term (2) expansivity, compressibility, heat capacity, and density of the solution in the sample cell). For an analyte dissolved in water, each $\mu$J per $\mu$L of absorbed energy should result in a pressure change of about ca. 135 mPa, and thus is detectable by a piezoelectric transducer available from Airmar or Stavely. The minimum pulse energy to reach the pulse threshold of a conventional piezoelectric transducer (i.e., about 1 mPa) can be estimated when the solution absorbance and the excitation volume are known.

A light beam (or other excitation beam) is directed to the sample cell of the sample array vessel. The light beam travels into the sample in the sample cell. An acoustic wave created by absorption of energy by the sample in the sample cell is then emitted from the sample and may be detected by an acoustic detector. For example, a light path as shown in FIG. 16 may be used. A light beam B is emitted from a light source (not shown) of a PAS system substantially perpendicular to an upper surface of the sample cell. The light beam B travels into and through the sample S. If the sample array vessel includes or is being used in conjunction with a reflective plate (see, e.g., FIG. 19), the light beam B is reflected back through the sample by the reflective plate. An acoustic wave created by absorption of energy by the sample is then emitted from the sample and is detected by an acoustic detector 48 positioned, e.g., as an air-coupled detector, directly beneath the sample cell or positioned in any other of the variety of acoustically suitable locations.

Another light beam path example is illustrated in FIG. 20, using a transmissive array. A light beam B is directed from a light source (not shown) at an angle θ into and refracts through sample S (retained in a sample cell C) and through a support past an acoustic detector D. Angle θ may be less than the critical angle $θ_c$ (known by those persons skilled in the art) to less than about 90° and is preferably at an angle of about 45°. An acoustic wave emitted from the irradiated sample S travels to the detector D. With such an embodiment, the light beam B is directed to avoid the detector D.

Figure 21:
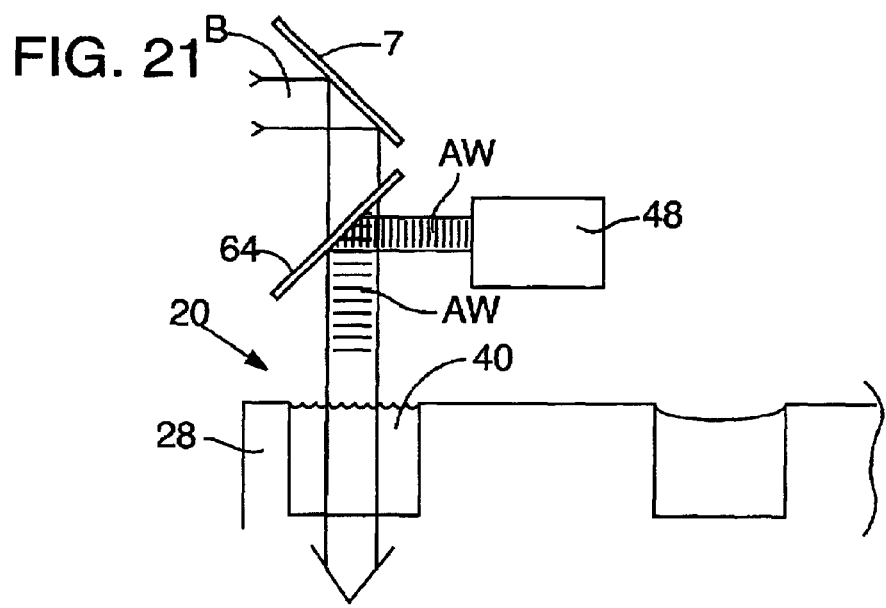
FIG. 21 shows an embodiment of a sample array vessel having air-coupled acoustic detection.

With reference to FIG. 21, in yet another example, a light beam B may be directed from a light source (not shown) in a direction substantially perpendicular to an upper surface of the sample array vessel 20 (or an optical reflector 7 may be used to direct the light beam B from a PAS system in such a direction). The light beam B is transmitted through a sample in a sample cell 40. An acoustic wave AW created by absorption of energy by the sample in the sample cell 40 is then transmitted to the air above the sample cell and is preferably reflected by an acoustic reflector 64 to an acoustic detector 48. In this embodiment, the acoustic reflector 64 transmits the excitation light beam B and reflects the acoustic waves AW.

Figure 22:
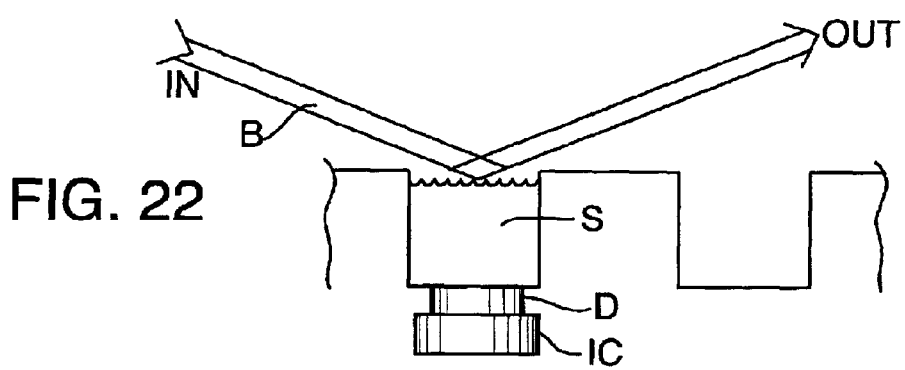
FIG. 22 shows a portion of an embodiment of a sample array vessel comprising a reflective array, each sample cell including a detector positioned thereunder.

With reference to FIG. 22, in yet another example, a light beam B is directed from a light source (not shown) in a direction substantially parallel to an upper surface of the sample array, at an angle greater than the critical angle, $θ_c$. The light beam B is reflected substantially (i.e., to produce total internal reflection "TIR") back through a sample S (within a sample cell). The acoustic waves created by absorption of energy by the sample S may then be transmitted through a lower surface of the sample cell to an acoustic detector D positioned beneath the sample cell. Clearly, a PAS system used with a sample array may direct the light beam to a sample in a variety of manners (in addition to those outlined herein). With the arrangements set forth in FIGS. 21 and 22, the light beams avoid impinging upon the detectors.

To analyze photoacoustic waveform data obtained from the transducers a statistical concept of a histogram may be used as described in U.S. Pat. No. 6,253,162, which is incorporated herein by reference.

The acoustic detectors used with the sample array vessels are preferably calibrated prior to use for detection of acoustic signals generated by analytes present within samples in the sample array vessel. A calibration method may comprise, for example, use of a standard solution or use of the acoustic detector itself in a pulse-echo mode. Specifically, a voltage is applied to the detector. The detector then expands, creating pressure within the detector and thus generates an acoustic wave that travels into the sample array vessel. The acoustic detector then detects the acoustic wave absorbed by and transmitted by the sample array vessel.

Alternatively, the acoustic detectors may be calibrated using a detector contact method. First, contact is made between the acoustic detector and the sample array vessel. Second, a standardized acoustic signal is generated. Third, the detector contact is adjusted until the desired electrical signal is obtained. Alternatively, the electrical signal may be detected and recorded for later analysis and normalization (as known to those persons skilled in the art). A standard acoustic signal may be generated, e.g., by directing a pulsed light onto and exposing a black or colored spot (e.g., carbon black) formed on the upper or lower surface of the sample array vessel (depending upon the sample array vessel and the position of the acoustic detector being used therewith).

A tapper calibration method may instead be used to calibrate the acoustic detectors. With the tapper method, a reproducible force to generate an acoustic wave or signal taps the sample array vessel. The detector is then used to detect the signal. The sample array vessel or detector may be adjusted when calibrating using these methods (if the data is not just normalized later) by, e.g., adjusting the tension holding the detector in contact with the sample array or by other suitable means as known to those persons skilled in the art.

Whereas the invention has been described with reference to multiple embodiments of the apparatus and representative methods, it will be understood that the invention is not limited to those embodiments and representative methods. On the contrary, the invention is intended to encompass all modifications, alternatives, and equivalents as may be included within the spirit and scope of the invention as defined by the appended claims.

What is claimed is:

1. A photoacoustic spectroscopy sample array vessel, comprising:
   a microtiter plate having multiple wells for holding samples; and
   at least one transducer acoustically coupled to the microtiter plate for detecting acoustic signals generated by analytes in the multiple samples.

2. The sample array vessel of claim 1, including at least 24 wells in the microtiter plate.

3. The sample array vessel of claim 1, including at least 384 wells in the microtiter plate.

* * * * *

UNITED STATES PATENT AND TRADEMARK OFFICE
CERTIFICATE OF CORRECTION

PATENT NO.        : 6,873,415 B2                                          Page 1 of 1
APPLICATION NO. : 10/002624
DATED             : March 29, 2005
INVENTOR(S)       : James E. Amonette et al.

It is certified that error appears in the above-identified patent and that said Letters Patent is hereby corrected as shown below:

<u>On the Cover Page, col. 2, line 5,</u>
Under FOREIGN PATENT DOCUMENTS, "WO 92 21973  10/1992" should read -- WO 92 21973  12/1992 --

Column 5, line 20, "$k_1$" should read -- $k_i$ --
Column 10, line 33, "thereof In" should read -- thereof. In --

Signed and Sealed this

Eleventh Day of July, 2006

JON W. DUDAS
*Director of the United States Patent and Trademark Office*